United States Patent [19]
Trent et al.

[11] Patent Number: 5,545,524
[45] Date of Patent: Aug. 13, 1996

[54] COMPOSITIONS AND METHODS FOR CHROMOSOME REGION-SPECIFIC PROBES

[75] Inventors: Jeffrey M. Trent; Paul S. Meltzer, both of Ann Arbor, Mich.

[73] Assignee: The Regents of the University of Michigan, Ann Arbor, Mich.

[21] Appl. No.: 101,600

[22] Filed: Aug. 3, 1993

Related U.S. Application Data

[63] Continuation-in-part of Ser. No. 821,954, Jan. 16, 1992, abandoned, and a continuation-in-part of PCT/US92/10429, Dec. 3, 1992, which is a continuation-in-part of Ser. No. 802,364, Dec. 4, 1991, abandoned.

[51] Int. Cl.$^6$ .............................. C12Q 1/68; C12P 19/34
[52] U.S. Cl. ........................ 435/6; 435/91.1; 435/91.2; 435/810; 436/501; 536/22.1; 536/23.1; 536/24.3; 536/24.31; 536/24.32; 536/24.33; 935/77; 935/78; 935/88
[58] Field of Search .............................. 435/6, 91.1, 91.2, 435/810; 436/501; 536/22.1, 23.1, 24.3–2.33; 935/77, 78, 88

[56] References Cited

FOREIGN PATENT DOCUMENTS

WO90/08821  8/1990  WIPO.

OTHER PUBLICATIONS

Guan et al., "Isolation of probes for a region of chromosome 6 deleted in malignant melanoma by chromosome microdissection" *Proceedings of the American Association for Cancer Research*, 82nd Annual Meeting, Houston, Texas (May 15–18, 1991) 32:302 (abstract no. 1795).

Taylor et al., "Visualisation of diagnostic tumour chromosome aberrations using fluorescence in *situ* hybridisation" Eleventh International Workshop On Human Gene Mapping, London, England, (Aug. 18–22, 1991), *Cytogenet Cell Genet.* (1991) 58: (1–4):2154, Abstract number 27372.

Cremer, T. et al., "Detection of chromosome aberrations in metaphase and interphase tumor cells by in situ hybridization using chromosome–region specific library probes." *Hum. Genet.* 80:235–246 (1988).

Bronstein, I. et al., "Rapid and Sensitive Detection of DNA in Southern Blots with Chemiluminescence." *Bio Techniques* 8:310–314 (1990).

Traver, C. N. et al., "Rapid Screening of a Human Genomic Library in Yeast Artificial Chromosomes for Single–Copy Sequences." *PNAS, USA* 86:5898–5902 (1989).

Hadano S. et al., "Laser Microdissection and Single Unique Primer Allow Generation of Regional Chromosome DNA Clones from a Single Human Chromosome." *Genomics* 11:364–373 (1991).

Lichter, P. et al., "Florescence in situ hybridization with Alu and L1 Polymerase Chain Reaction Probes for Rapid Characterization of Human Chromosomes in Hybrid Cell Lines." *PNAS USA* 87:6634–638 (1990).

Hampton et al., "Characterization and mapping of microdissected genomic clones from the adenomatous polyposis coli (APC) region" *Genomics* (1991) 11:247–251.

Johnson, "Molecular cloning of DNA from specific chromosomal regions by microdissection and sequence–indepepndent amplification of DNA" *Genomics* (1990) 6:243–251.

(List continued on next page.)

*Primary Examiner*—W. Gary Jones
*Assistant Examiner*—Ardin H. Marschel
*Attorney, Agent, or Firm*—Morrison & Foerster

[57] ABSTRACT

The present invention provides a rapid reproducible method for generating chromosome region-specific probes for diagnostic and research applications. The method of the present invention comprises microdissecting a chromosome of interest to produce a DNA fragment, treating the dissected DNA fragment with topoisomerase I, amplifying the treated dissected DNA fragment and labelling the amplified DNA. By utilizing the method of the present invention, region-specific probes for fluorescence in situ hybridization (FISH) from a single microdissected chromosome may be generated.

18 Claims, 3 Drawing Sheets

OTHER PUBLICATIONS

Kuo et al., "Detection of aneuploidy involving chromosomes 13, 18, or 21, by fluorescence in situ hybridization (FISH) to interphase and metaphase amniocytes" *Am. J. Hum. Genet.* (1991) 49:112–119.

Kuwano et al., "Detection of deletions and cryptic translocations in Miller–Dieker syndrome by in situ hybridization" *Am. J. Hum. Genet.* (1991) 49:707–714.

Lengauer et al., "Painting of defined chromosomal regions by in situ suppression hybridizaion of libraries from laser-–microdissected chromosomes" *Cytogenet. Cell. Genet.* (1991) 56:27–30.

Lichter et al., "Delineation of individual human chromosomes in metaphase and interphase cells by in situ suppression hybridization using recombinant DNA libraries" *Hum. Genet.* (1988) 80 224–234.

Pinkel et al., "Fluorescence in situ hybridization with human chromosome-specific libraries: detection of trisomy 21 and translocations of chromosome 4" *Proc. Natl. Acad. Sci. USA* (1988) 85:9138–9142.

Tkachuk et al., "Detection of bcr–abl fusion in chronic myelogenous leukemia by in situ hybridization" *Science* (1990) 250:559–562.

Trautmann et al., "Detection of APC region-specific signals by nonisotopic chromosomal in situ suppression (CISS)–hybridization using a microdissection library as a probe" *Hum. Genet.* (1991) 87:495–497.

Callen et al., "Chromosomal origin of small ring marker chromosomes in man: characterization by molecular genetics" *Am. J. Hum. Genet.* (1991) 48:769–782.

Meese et al., "Development and utilization of a somatic cell hybrid mapping panel to assign NotI linking probes to the long arm of human chromosome 6" *Genomics* (1992) 12: 542–548.

Fearon et al., "A genetic model for colorectal tumorigenesis" *Cell* (1990) 61:759–767.

Millikin et al., "Loss of heterozygosity for loci on the long arm of chromosome 6 in human malignant melanoma" *Cancer Res.* (1991) 51:5449–5453.

Mitelman et al., "Report of the committee on chromosome changes in neoplasia" *Cytogenet. Cell Genet.* (1991)00:000–000. A pre-print copy was previously submitted.

Nowell et al., "Chromosome translocations and oncogenes in human lymphoid tumors" *Am. J. Clin. Pathol.* (1990) 94:229–237.

Pathak et al., "Involvement of chromosome 6 in rearrangements in human malignant melanoma cell lines" *Cytogenet. Cell. Genet.* (1983) 36:573–579.

Rowley, "Molecular cytogenetics: Rosetta Stone for understanding cancer–twenty–ninth G.H.A. Clowes Memorial Award Lecture" *Cancer Res.* (1990) 50:3816–3825.

Trent et al., "Chromosome 6q involvement in human malignant melanoma" *Cancer Genet. & Cytogenet.* (1983) 9:177–180.

Trent et al., "Relation of cytogenetic abnormalities and clinical outcome in metastatic melanoma" *New Eng. J. Med.* (1990) 322:1508–1511.

Trent et al., "Tumorigenicity in human melanoma cell lines controlled by introduction of human chromosome 6" *Science* (1990) 247:568–571.

Fountain et al., "Physical mapping of a translocation breakpoint in neurofibromatosis" *Science* (1989) 244:1085–1087.

Warburton, "*De novo* balanced chromosome rearrangements and extra marker chromosomes identified at prenatal diagnosis: clinical significance and distribution of breakpoints" *Am. J. Hum. Genet.* (1991) 49:995–1013.

Haluska et al., "Oncogene activation by chromosome translocation in human malignancy" *Ann. Rev. Genet.* (1987) 21:321–345.

Weinberg, "A short guide to oncogenes and tumor–suppressor genes" *J. NIH Res.* (1991) 3:45–47.

Gelehrter et al., eds., *Principles of Medical Genetics* (1990) Williams & Wilkins, Baltimore, Maryland, pp. 156–189.

Hassold, "Chromosome abnormalities in human reproductive wastage" *Trends in Genet.* (Apr. 1986) pp. 105–110.

Wesley et al., "Cloning regions of the *Drosophila* genome by microdissection of polytene chromosome DNA and PCR with nonspecific primer" *Nucleic Acids Res.* (1989) 18:599–603.

Cotter et al., "Gene mapping by microdissection and enzymatic amplification: heterogeneity in leukaemia associated breakpoints on chromosome 11" *Genes, Chromosomes & Cancer* (1991) 3:8–15.

Han et al., "Direct amplification of a single dissected chromosomal segment by polymerase chain reaction: a human brain sodium channel gene is on chromosome 2q22–q23" *Proc. Natl. Acad. Sci. USA* (1991) 88:335–339.

Ricciardi et al., "Purification and mapping of specific mRNAs by hybridization–selection and cell–free translation" *Proc. Natl. Acad. Sci. USA* (1979) 76:4927–4931.

Hochgeschwender et al., "Construction and screening of a genomic library specific for mouse chromosome 16" *Proc. Natl. Acad. Sci. USA* (1989) 86:8482–8486.

Senger et al., "Microdissection of banded human chromosomes" *Hum. Genet.* (1990) 84:507–511.

Chehab et al., "Detection of specific DNA sequences by florescence amplification: a color complementation assay" *Biochem.* (1989) 86:9178–9182.

Lüdecke et al., "Cloning defined regions of the human genome by microdissection of banded chromosomes and enzymatic amplification" *Nature* (1989) 338:348–350.

COMPOSITIONS AND METHODS FOR CHROMOSOME REGION-SPECIFIC PROBES

RELATED APPLICATIONS

This is a continuation-in-part of U.S. application Ser. No. 07/821,954, entitled "Method for Generating Chromosome Region-Specific Probes," filed Jan. 16, 1992, by Trent et al., now abandoned, and of International Application Number PCT/US92/10429, entitled "Method for Generating Chromosome Region-Specific Probes" filed Dec. 3, 1992 by Trent et al., which are continuation-in-part applications of U.S. application Ser. No. 07/802,364, entitled "Method for Generating Chromosome Region-Specific Probes" filed Dec. 4, 1991, by Trent et al., now abandoned.

Research related to the present invention was supported in part by the National Institutes of Health PHHS grants CA-29476 and CA-41183 and the National Institutes of Health Genome Center Grant HG-00209. The government may have certain rights to this invention.

FIELD OF THE INVENTION

The present invention relates generally to chromosome region-specific probes and their preparation and use. More specifically, the present invention relates to a method of generating chromosome region-specific probes through amplification of treated microdissected chromosomal DNA, the probes generated thereby and methods of their use.

BACKGROUND OF THE INVENTION

The identification and analysis of chromosome abnormalities is of great clinical and research importance. Chromosome abnormalities are a significant cause of congenital malformation and are responsible for at least half of spontaneous abortions or miscarriages. Hassold, T., *Trends Genet.* 2:105 (1986); deGrouchy, J. et al., *Clinical Atlas of Human Chromosomes* (John Wiley & Sons, New York, 2d ed, 1984); Gardner, R. et al., *Chromosome Abnormalities and Genetic Counseling* (Oxford Univ. Press, New York, 1989); Gelehrter, T. et al. *Principals of Medical Genetics* (Williams & Wilkins, Baltimore, Md., 1990) pp. 159–189. The analysis of recurring chromosome abnormalities in malignant cells has also become an integral part of the diagnostic and prognostic workup of many human cancers. Heim, S. et al., Cancer Cytogenetics (A. Liss, New York, 1987); Sandberg, A., *The Chromosomes in Human Cancer and Leukemia* (Elsevier, New York, 1990); Trent, J. et al., *New Eng. J. Med.* 322:1508 (1990). In addition to these clinical applications, the molecular examination of chromosome abnormalities has facilitated the identification of genes related to the pathogenesis of both hereditary diseases and cancer. Haluska, F. et al., *Ann. Rev. Genet.* 21:321 (1987); Weinberg, R., *J. NIH Res.* 3:45 (1991); Nowell, P. et al., *Am. J. Clin. Pathol.*, 94:229 (1990); Rowley, J., *Cancer Res.* 50:3816 (1990); Fearon, E. et al., *Cell* 61:759 (1990); Fountain, J., *Science* 244:1085 (1989).

Current cytogenetic techniques for chromosome analysis are not, however, entirely satisfactory. One major technical limitation is their inability to unequivocally characterize all cytologically recognizable chromosome rearrangements. For example, amniocentesis may reveal unidentifiable de novo unbalanced translocations or unknown supernumerary marker chromosomes. Warburton, D., *J. Hum. Genet.* 49:995 (1991); Callen, D. et al., Am *J. Hum. Genet.* 48:769 (1991). Likewise, in many human cancers, particularly solid tumors, the presence of unidentifiable marker chromosomes or unidentifiable unbalanced translocations frequently prevents complete karyotypic analysis. Mitelman, F., *Catalog of Chromosome Aberrations in Cancer* (Wiley-Liss, New York, ed. 4th ed, 1991); Mitelman, F. et al., *Cytogenet. Cell Genet.* 58:1053–1079 (1991).

Chromosome microdissection has become a powerful approach to generate chromosome band-specific libraries and fluorescence in situ hybridization (FISH) probes for physical mapping or cytogenetic analysis. Ludecke, H. J. et al., *Nature* 338:348–350 (1989); Senger, G. et al., *Hum. Genet.* 84:507–511 (1990); Kao, F. T., et al., *PNAS (USA)* 88:1844–1848 (1991); Guan, X. Y. et al., *Genomics* 14:680–684 (1992); Hirota, T. et al., *Genomics* 13:349–354 (1992); Meltzer, P. S. et al., *Nature Genet.* 1:24–28 (1992) and Deng, H. X. et al., *Hum. Genet.* 89:13–17 (1992). The generation of chromosome region-specific painting probes by polymerase chain reaction (PCR) amplification of microdissected DNA (termed to "Micro-FISH" in Meltzer, P. S. et al., *Nature Genet.* 1:24–28 (1992) and referred to such herein) has proven useful in solving problems in cytogenetic analysis which are indeterminant by routine chromosome banding analysis, e.g. marker chromosomes. Any abnormal chromosome segment can be microdissected and converted to a FISH probe for hybridization to normal metaphase chromosomes, resulting in a pattern of hybridization which reveals its chromosomal derivation. Meltzer, P. S. et al., *Nature Genet.* 1:24–28 (1992) and Deng, H. X. et al., *Hum. Genet.* 89:13–17 (1992). Using this approach, which has been called "reverse chromosome painting," it has been demonstrated that a series of chromosomes with apparent terminal deletions were actually cryptic unbalanced translocations. Meltzer, P. S. et al., *Nature Genet.* (in press) (1993).

In principle, Micro-FISH has made it possible to identify the chromosomal constitution of any cytologically visible chromosome rearrangement. However, previously published microdissection techniques have included the time-consuming and labor-intensive requirement of dissecting 20–40 DNA fragments from a target region in order to obtain sufficient template for PCR amplification. Guan, X. Y. et al., *Genomics* 14:680–684 (1992)and Meltzer, P. S. et al., *Nature Genet.* 1:24–28 (1992). Several hours are required for the microdissection procedure, and with the addition of each copy to the collection drop, the probability of extraneous DNA contamination is increased. The contaminating DNA may derive from the glass microneedle which touches DNA other than target DNA, or could be introduced into the collection drop from the air when the tube is repeatedly opened and closed. DNA contamination is a critical problem in the amplification of dissected DNA because the initial amount of dissected material is exceedingly small (in the range of $10^{-13}$ to $10^{-14}$ g/fragment). Accordingly, even minute amounts of contaminating DNA can overwhelm the microdissected DNA leading to a useless amplification product. Unfortunately, decreasing the copy number of dissected DNA fragments tends to reduce the complexity and, therefore, the signal intensity of the resulting FISH probe.

It would thus be desirable to provide a method of generating region-specific probes for any chromosome band or region. It would further be desirable that the method for the preparation of such probes be relatively simple, rapid and reproducible. It would also be desirable to provide a method wherein a large number of highly specific probes could be easily generated. It would further be desirable to provide a method of generating region-specific probes which decreases the number of microdissected chromosme fragments required for probe generation. It would also be desirable to provide a method of generating region-specific probes which requires less time and labor than is required in current methods. It would further be desirable to provide a method of generating region-specific probes which reduces the risk of exogenous DNA contamination. It would also be desirable that probes generated by this method provide means for identifying all cytologically recognizable chromosomal rearrangements and deletions. It would further be desirable to provide a method of screening genomic, recombinant or other DNA libraries with a region-specific probe.

SUMMARY OF THE INVENTION

The present invention comprises a simple rapid method for generating chromosome region-specific probes, the probes generated thereby and their use in clinical and research applications. The method of generating a chromosome region-specific probe generally comprises the microdissection and enzymatic amplification of chromosomal DNA from the chromosomal region of interest, and labelling of the amplified DNA. The amplification is carried out by polymerase chain reaction (PCR) and may be primed by an oligonucleotide primer of random degenerate nucleotides, i.e. universal primer. The method of the present invention further comprises the step of treating the microdissected chromosome fragments with an enzyme, specifically topoisomerase I (Topo I), before PCR. The treatment with Topo I dramatically increases the efficacy of amplification, thereby reducing the number of dissected DNA fragments required to generate the probes of the present invention. By reducing the number of copies of dissected DNA fragments, the time-consuming and labor-intensive aspects of microdissection are also reduced as well as the risk of contamination during the microdissection process.

Other features and advantages of the present invention will become apparent from the following description and appended claims, taken in conjunction with the accompanying drawings.

BRIEF DESCRIPTION OF THE DRAWINGS

The various advantages of the present invention will become apparent to one skilled in the art by reading the following specification and subjoined claims and by referencing the following drawings in which:

DETAILED DESCRIPTION OF THE PREFERRED EMBODIMENTS

Figure 1:
FIG. 1 illustrates the effects of Topo I on PCR products comparing microdissected DNA from one copy of 18p11.1-p11.3.

The method of generating chromosome region-specific probes of the present invention generally comprises the PCR amplification of treated microdissected chromosomal fragments, and labelling of the amplified DNA. By "treated" is meant the dissected chromosome fragment(s) are treated with topoisomerase I (Topo I) prior to PCR amplification. As used herein, "DNA" collectively refers to DNA or cDNA unless otherwise indicated. By "amplified DNA" is meant the DNA sequence(s) generated or amplified from the microdissected region.

By treating the dissected DNA fragment with Topo I, which catalyzes the relaxation of supercoiled DNA, single microdissected chromosome fragments may be used to generate region-specific probes. Liu, L. F. et al., *PNAS (USA)* 84:7024–7027 (1987); Wang, J. D., *Biochem. Biophys. Acta.* 909:1–9 (1987) and D'Arpa, P. et al., *Biochem. Biophys. Acta.* 989:163–177 (1989). The method of the present invention thus reduces the number of copies of dissected DNA fragments required to produce region-specific probes. By reducing the number of copies of dissected DNA fragments, probe preparation is simplified, expedited and accelerated. The method of the present invention thus generates high intensity region-specific probes, while significantly decreasing the time-consuming and labor-intensive aspects of microdissection. The reduction of the number of copies required to generate a useful probe also significantly decreases the risk of contamination by foreign DNA during the microdissection process. This will allow microdissection to be more widely used in the cytogenetic analysis of chromosome rearrangements in both cancer and hereditary diseases. In addition, the method of the present invention makes it possible to construct a series of non-overlapping band-specific DNA microclone libraries to provide complete coverage of individual chromosomes for physical mapping.

Probes generated by the methods of the present invention can be used as whole chromosome or region-specific probes for clinical and research purposes and provide a direct link between cytogenetic and physical mapping techniques. They enable the analysis of any unknown chromosome regions and chromosomal alterations. The probes of the present invention are also ideally suited for gene isolation procedures, particularly where there is reason to suspect that a given gene is located in a specific chromosome band or region.

Although it is difficult to model the exact effect of Topo I on the dissected DNA fragments, because the fixed, stained, microdissected chromosome fragments are certainly different from native chromatin, it is likely that the highly supercoiled conformation of DNA in a condensed metaphase chromosome impairs access of primer and DNA polymerase to the template. Structural constraints may persist even after incubation of the microdissected chromosome at denaturing temperatures. By promoting relaxation of the template DNA, Topo I treatment may result in a more open structure after heat denaturation thereby facilitating the formation of initiation complexes. Such an effect is consistent with the proposed role of Topo I in DNA replication and in chromosome puffing in *Drosophila*. Fleischmann, G. et al., *PNAS(USA)*81:6958–6962(1984). Also, it has been found that treating microdissections with or without Proteinase K has no apparent effect on probe quality.

The step of enzymatic amplification of the microdissected DNA of the present invention is carried out by the polymerase chain reaction (PCR) using *Thermus aquaticus* (taq) polymerase or any other of a number of thermostable enzymes from other sources, such as DNA polymerase from *Thermus flavus, Theremus thermophilus*, and the like. Additionally, one to four cycles of "preamplification" with a non-thermophilic DNA polymerase such as T7 DNA polymerase or Klenow fragment of *E. coil* DNA polymerase can be carried out before PCR. The introduction of "preamplification" with T7 DNA polymerase has resulted in increased efficiency of amplification and fluorescence signal intensity presumably because the lower reaction temperature promotes successful priming at shorter stretches of primer annealing. Bohlander, S. K. et al., *Genomics* 13:1322–1324

(1992) and Zhang, J. et al., *Blood* (in press) (1993). However, it has not been possible to obtain high quality probes routinely with less than 10 microdissected copies. This suggests that although in principle degenerate oligonucleotide primed PCR would be expected to result in recovery of sequences from a single microdissected chromosome, the complexity of the resultant PCR product is insufficient to generate a strong fluorescence signal.

In an embodiment of the method of the present invention, a DNA oligonucleotide primer is used to directly prime DNA synthesis at intervals along the microdissected DNA template. In this scheme, a "universal" primer of random degenerate nucleotides is preferred, although an Alu or other PCR-based primer strategy can also be utilized. It will also be appreciated that the primer sequence may be altered to increase PCR yield, to enhance signal strength or to facilitate cloning of the PCR product for large scale production.

The probes of the invention can also be labelled using any conventional techniques and labels which provide a detection scheme. Examples of suitable labelling schemes include biotin-avidin immunofluorescence, chromogenic and radioisotopic (e.g. $^3$HTdR) labelling and direct chemical labelling with fluorochromes. Fluorescent biotin-based labels such as biotin-16-dUTP are preferred.

The following Specific Example further describes the present invention.

SPECIFIC EXAMPLE

Materials and Methods

Microdissection.

The procedure for chromosome microdissection was performed essentially as described previously in Guan, X. Y. et al., *Genomics* 14:680–684 (1992) and Meltzer, P. S. et al., *Nature Genet.* 1:24–28 (1992). Basically, 1 to 5 copies of a targeted chromosomal region were dissected from GTG-banded metaphase chromosomes derived from phytohemagglutinin (PHA)-stimulated human peripheral blood lymphocytes. The microdissection was performed with a glass microneedle controlled by a micromanipulator attached to an inverted microscope.

Topoisomerase I Treatment and Amplification of Dissected DNA.

The dissected chromosome fragments were transferred to a 5 μl collection drop (containing 40 mM tris-HCl, pH 7.5, 20 mM MgCl$_2$, 50 mM NaCl, 200 μM of each dNTP, 1 unit Topo I (Promega), and 5 pmol of a universal primer (CCGACTCGAGNNNNNNATGTGG). Telenius, H. et al., *Genomics* 13:718–725 (1992). After the desired number of dissected DNA fragment(s) were collected, the collection drop was covered with a drop of mineral oil and incubated at 37° C. for 30 min, followed by incubation at 96° C. for 10 min.

An initial 8 cycles of PCR (denaturation at 94° C. for 1 min, annealing at 30° C. for 2 min, and extension at 37° C. for 2 min) was conducted by adding approximately 0.3 units of T7 DNA polymerase (Sequenase version 2.0, USB) at each cycle. Sequenase (13 units/μl) was diluted 1 to 8 in enzyme dilution buffer (USB) and 0.2 μl was added to 5 μl reaction mixture. Bohlander, S. K. et al., *Genomics* 13:1322–1324 (1992) and Zhang, J. et al., *Blood* (in press) (1993). Following the pre-amplification step, a conventional PCR reaction catalyzed by Taq DNA polymerase was performed in the same tube. Fifty/μl PCR reaction mixture (10 mM Tris-HCl, pH 8,4, 2 mM MgCl$_2$, 50 mM KCl, 0.1 mg/ml gelatin, 200 μM each of dNTP, and 2 units Taq DNA polymerase (Perkin-Elmer/Cetus)) was added directly to the reaction tube. The reaction was heated to 95° C. for 3 min followed by 35 cycles as 94° C. for 1 min, 1 min at 56° C., 2 min at 72° C., with a 5 min final extension at 72° C.

Fluorescent In Situ Hybridization (FISH).

Amplified microdissected DNA (2 μl) was labeled with Biotin-16-dUTP (BMB) in a secondary PCR reaction identical to that described above except for the addition of 20 μM biotin-16-dUTP. The reaction was continued for 12–16 cycles of 1 min at 94° C., 1 min at 56° C., and 2 min at 72° C., with a 5 min final extension at 72° C. The PCR products were then purified with a Centricon 30 (Amicon) filter and used for FISH. Hybridization of the FISH probes followed previously described procedure (Meltzer, P. S. et al., *Nature Genet.* 1:24–28 (1992)), which is based upon the procedure of Pinkel et al., *PNAS (USA)* 85:9138–9142 (1988). Basically, for each hybridization, approximately 100 ng of probe was added to 10 μl hybridization mixture (containing 55% formamide, 2×SSC, and 1 μl human Cot I DNA (BRL)) and denatured at 75° C. for 5 min. The slides with metaphase spreads were then denatured in 70% formamide, 2×SSC at 70° C. for 2 min, and hybridized with probes at 37° C. in a moist chamber overnight. The slides were then washed three times in 50% formamide, 2×SSC at 45° C. for 3 min each. The hybridization signal of the probe was detected by two layers of FITC-conjugated avidin (Vector) and amplified with one layer of anti-avidin antibody (Vector). Slides were counterstained with 0.5 μg/ml propidium iodide in an antifade solution and examined with a Zeiss Axiophot microscope equipped with a dual bandpass filter.

Results

Chromosome Microdissection.

The results of 10 experiments are set forth including three multicopy (3–5 copies) and seven single copy microdissections. The regions included in single copy experiments were 2p23-p25, 6q13-q21, 14q25-q26, 17p11.1-p13, 18p11.1-p11.3, 21q21-q22 and 22q11.

Topoisomerase I Treatment and PCR Amplification.

In three multi-copy experiments, as well as three experiments using only a single copy of a chromosome band, side by side comparison was made between the probes generated with and without Topo I treatment. In all six experiments useful probes were generated only in the Topo I treated reactions. This demonstration of enhanced amplification was documented both by analyzing PCR products on 1% agarose gels (FIG. 1), as well as by FISH analysis of PCR products (FIGS. 2A–2D and FIGS. 3A–3F).

FIG. 1 illustrates an ethidium bromide stained 1% agarose gel displaying PCR products from the single copy microdissection of 18p11.1-p11.3. The left most lane contains size markers in base pairs. Lanes 1 and 2 of FIG. 1 show PCR reaction with no added DNA; lanes 3 and 4 show PCR products of 5 ng human DNA, and lanes 5 and 6 show single dissected chromosome fragment of 18p11.1-p11.3. The reactions of lanes 2, 4, and 6 were treated with Topo I.

As shown in FIG. 1, lanes 1 and 2, there was no apparent DNA amplification in the negative control lanes (no DNA) whether or not Topo I was included while an intense smear was produced in the positive control. This suggests that the Topo I preparation utilized was free of DNA contamination as well as PCR inhibitors. The microdissection PCR products demonstrate a marked effect of Topo I treatment on the resulting products of two different single copy dissections of 18p. Specifically, PCR products from the Topo I treated dissected DNA appear as a smear ranging from 200–650 base pairs (see FIG. 1, lane 6). In contrast, the quantity of PCR product generated without Topo I treatment remained below the sensitivity of ethidium bromide staining. These results suggest that Topo I increases the yield of the PCR reaction.

Figure 2A:
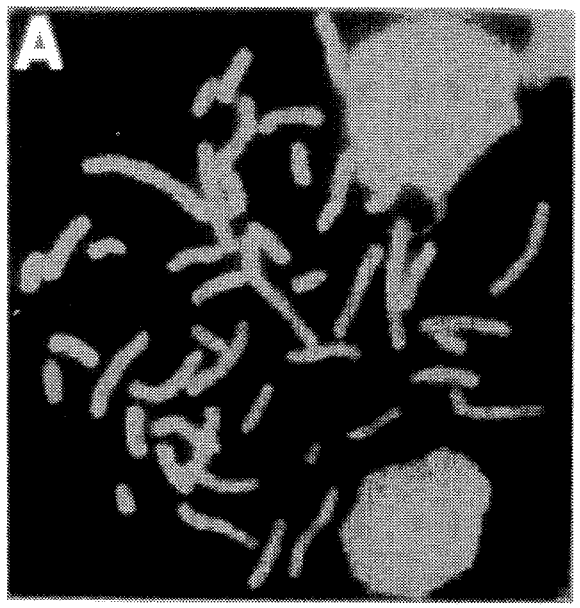
FIGS. 2A–2D illustrate the results of Topo I treatment on fluorescence signal intensity.
Figure 2B:
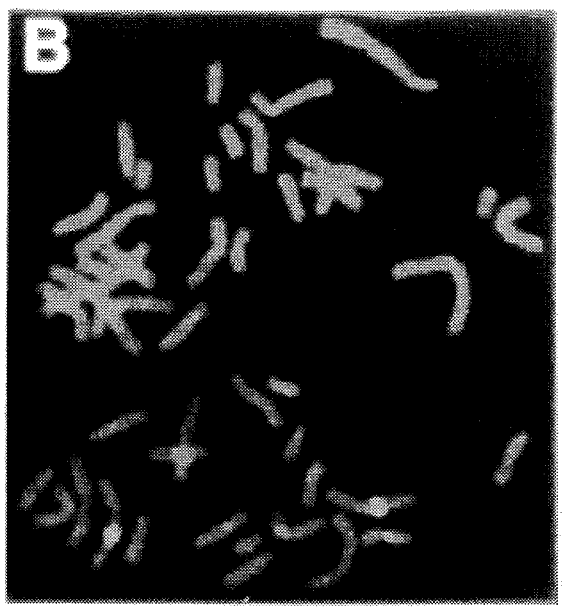
Figure 2C:
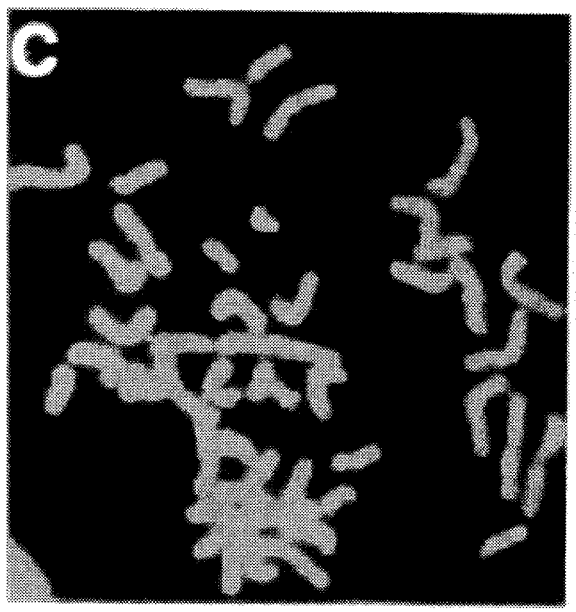
Figure 2D:
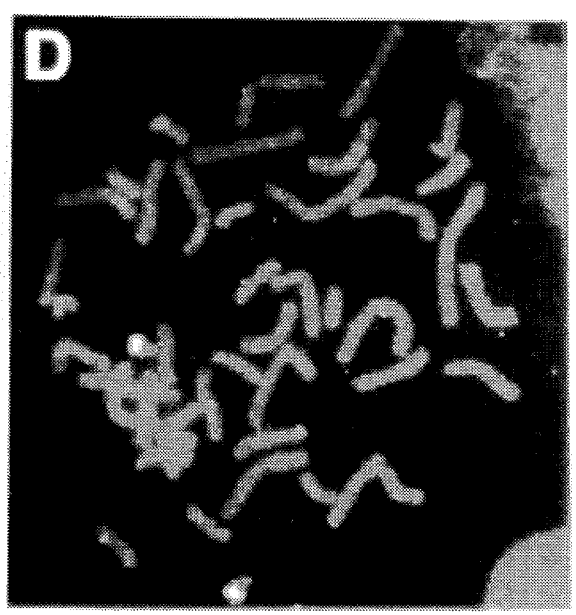

In order to verify this conclusion, the PCR products were tested by FISH analysis. For all of the six side-by-side comparisons (i.e. treatment of dissected DNA with or without Topo I before PCR amplification) FISH probes from Topo I treated dissected DNA showed intense fluorescence signals corresponding to the dissected region. FIGS. 2A–2D show examples of two of the six side-by-side comparisons. FIGS. 2A and 2B show FISH to normal metaphase chromosomes using 5 copies of 6q15-q16 without Topo I (FIG. 2A) or with Topo I (FIG. 2B) treatment. FIGS. 2C and 2D show FISH to normal metaphase chromosome using 3 copies of 22q11.2-q13 treated without (FIG. 2C) or with (FIG. 2D) Topo I. In all 6 experiments, detectible fluorescence signals corresponding to the dissected regions were generated only with probes from Topo I treated microdissections. In contrast, even though quantities of DNA detectible by ethidium bromide were generated in the secondary PCR labelling reaction, no useful fluorescence signals were observed using probes generated without Topo I treatment.

Fluorescent In Situ Hybridization.

Figure 3A:
FIGS. 3A–3F illustrate examples of Micro-FISH probes from six different single copy microdissections.
Figure 3B:
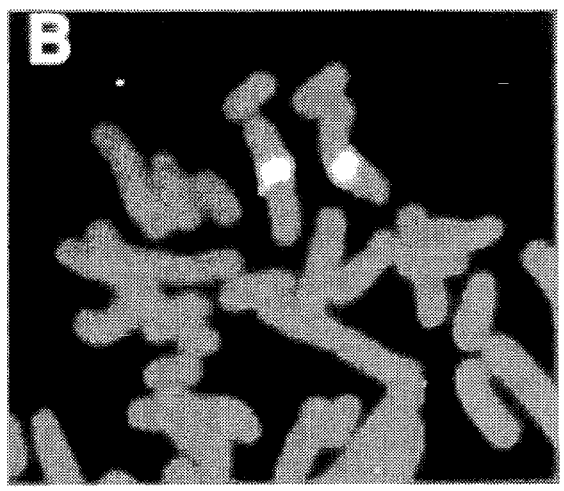
Figure 3C:
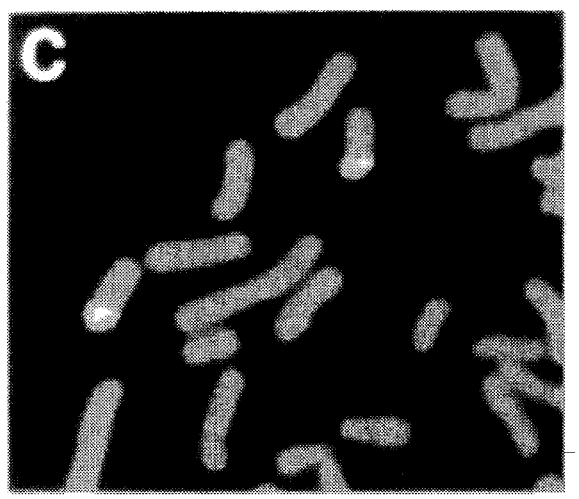
Figure 3D:
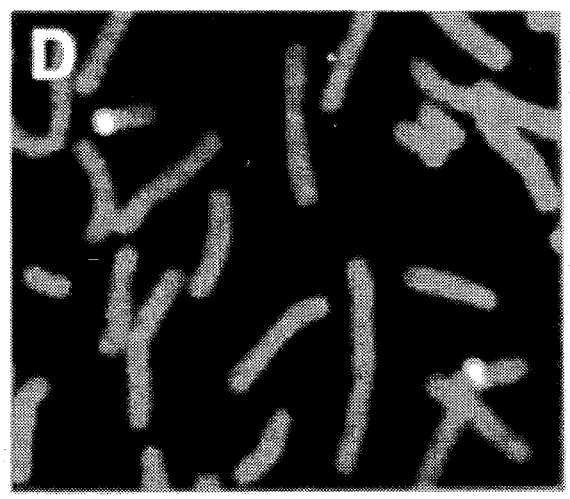
Figure 3E:
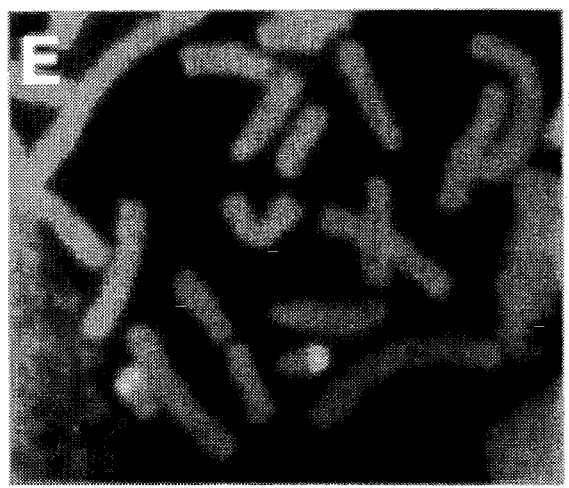
Figure 3F:
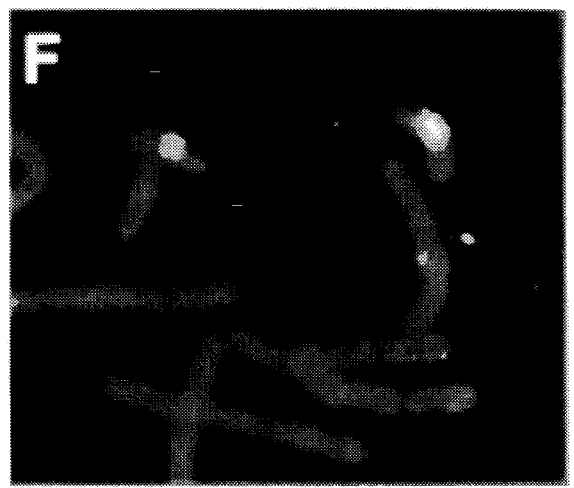

To demonstrate the general applicability of this methodology, FISH probes were generated from single copies of four additional regions treated with Topo I prior to PCR amplification. FIGS. 3A–3F show examples of six single copy probes hybridized to normal lymphocyte metaphase chromosomes documenting the signal intensity and regional specificity of these probes. The probes were prepared from Topo I treated single copy microdissections of the following regions: 2p23-p25 (FIG. 3A), 6p13-q21 (FIG. 3B), 17p11.1-p13 (FIG. 3C), 18p11.1-p11.3 (FIG. 3D), 21q21-q22 (FIG. 3E) and 22q11 (FIG. 3F). In all cases, the probes, labeled with Biotin-16-dUTP in a secondary PCR, hybridized specifically to the dissected region. A comparison of the signal intensity of the single copy dissection probes to previous Micro-FISH probes (derived from 20–40 microdissected copies), suggests that the fluorescence intensity provided by probes from single copy microdissection was comparable to that generated by multicopy probes. FIG. 3A illustrates a FISH result using the PCR product from the microdissection of a single copy of 2p23-p25 yielding a fluorescent signal that is of sufficient intensity that it can be visualized in interphase nuclei (results not shown).

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

All patent applications and publications cited herein are specifically incorporated by reference.

---

---

We claim:

1. A method of generating a chromosome region-specific nucleic acid probe for a chromosomal region of interest comprising the steps of:
   (a) microdissecting the chromosomal region of interest to provide a microdissected chromosome fragment;
   (b) treating the microdissected chromosome fragment with topoisomerase I; and
   (c) amplifying the treated microdissected chromosome fragment.

2. The method of claim 1, wherein the step of amplification further comprises a polymerase chain reaction.

3. The method of claim 1, further comprising the step of (d) labelling the amplified DNA.

4. The method of claim 1, wherein the step of amplification further comprises the steps of priming the amplification with the following sequence of nucleotides: CCGACTCGAGNNNNNNNATGTGG.

5. The method of claim 1, wherein the region of interest comprises a chromosome band.

6. The method of claim 1, wherein the chromosomal region of interest is in its normal chromosomal location.

7. The method of claim 1, wherein the chromosomal region of interest is translocated from its normal chromosomal location.

8. A nucleic acid probe produced by the method of claim 1.

9. The method of claim 3, wherein the label is fluorescent.

10. The method of claim 3, wherein the label is biotin-based.

11. The method of claim 1, wherein the nucleic acid probe is region-specific and further comprising the step of adding an effective amount of unlabeled repetitive DNA.

12. The method of claim 11, wherein the unlabeled repetitive DNA is human Cot I DNA.

13. A method of localizing a chromosomal region of interest in a chromosome sample having nucleic acid sequences, comprising the steps of:

(a) providing a chromosome region-specific probe generated by:
 (i) microdissecting the chromosomal region of interest to provide a microdissected chromosome fragment;
 (ii) treating the microdissected chromosome fragment with topoisomerase I;
 (iii) amplifying the microdissected chromosome fragment; and
 (iv) labelling the amplified fragment to provide the probe; and (b) contacting the chromosome sample with the probe under conditions favorable for hybridization between the probe and complementary nucleic acid sequences in the sample;

(c) determining the existence and location of hybridization in the chromosome sample.

14. The method of claim 13, wherein amplification is by a polymerase chain reaction.

15. The method of claim 13, wherein the label is fluorescent.

16. The method of claim 13, wherein the sample comprises a DNA library.

17. A method of screening a library of nucleic acid clones for a clone of a chromosomal region of interest comprising the steps of:

(a) providing a chromosome region-specific probe generated by:
 (i) microdissecting the chromosomal region of interest to provide a microdissected chromosome fragment;
 (ii) treating the microdissected chromosome fragment with topoisomerase I;
 (iii) amplifying the microdissected chromosome fragment; and
 (iv) labelling the amplified fragment to provide the probe;

(b) providing the library of clones to be screened;

(c) contacting each clone with the probe under conditions favorable for nucleic acid hybridization; and (d) determining whether and in which clone hybridization has occurred.

18. The method of claim 17, wherein the library of clones comprises a recombinant DNA library.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:1:

CCGACTCGAG      10